US00PP28624P3

(12) United States Plant Patent
NeSmith

(10) Patent No.: US PP28,624 P3
(45) Date of Patent: Nov. 14, 2017

(54) RABBITEYE BLUEBERRY PLANT NAMED 'T-460'

(50) Latin Name: *Vaccinium ashei*
Varietal Denomination: T-460

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 108 days.

(21) Appl. No.: 14/756,566

(22) Filed: Sep. 17, 2015

(65) Prior Publication Data

US 2017/0086344 P1 Mar. 23, 2017

(51) Int. Cl.
*A01H 5/08* (2006.01)

(52) U.S. Cl.
USPC ..... Plt./157

(58) Field of Classification Search
USPC ..... Plt./156, 157
See application file for complete search history.

(56) References Cited

PUBLICATIONS

NeSmith, Scott. 2011. Blueberry Cultivar Development at the University of Georgia: A progress report for 2005. http://www.smallfruits.org/blueberries/production/alap05Report.pdf. Accessed Mar. 28, 2017. 12 pages.*

* cited by examiner

*Primary Examiner* — Susan McCormick Ewoldt
*Assistant Examiner* — Karen Redden
(74) *Attorney, Agent, or Firm* — Klarquist Sparkman, LLP

(57) ABSTRACT

The new variety 'T-460' ripens around mid June in southern Georgia and early July in middle Georgia. The fruit of the new variety 'T-460' are large, with good scar and very good color. The new variety 'T-460' is moderately vigorous with an estimated chilling requirement of about 500 to 550 hours at or below approximately 7° C. The asexually reproduced variety is reliably propagated vegetatively.

5 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'T-460' is a rabbiteye blueberry plant that is a *Vaccinium ashei.*

Variety denomination: The new rabbiteye blueberry plant claimed is of the variety denominated 'T-460'.

BACKGROUND OF THE INVENTION

The present invention relates to the discovery of a new and distinct cultivar of rabbiteye blueberry plant botanically known as a *Vaccinium ashei* and herein referred to as 'T-460', as herein described and illustrated.

The new blueberry plant variety 'T-460' was selected in Tifton, Ga. in the mid 1980's. The new variety 'T-460' ripens around mid June in southern Georgia. The fruit of the new variety 'T-460' are large with good scar and very good color. The new variety 'T-460' has demonstrated self-fruitfulness and is moderately vigorous with an estimated chilling requirement of about 500-550 hours at or below 7° C.

Pedigree and history: 'T-460' was selected in the mid 1980's in Tifton, Ga., originating from a cross of 'T-223'× 'T-258'. 'T-223' is the maternal parent and 'T-258' is the paternal parent. Both parent 'T-223' and parent 'T-258' are non-patented breeding lines. The selection was first asexually propagated by softwood cuttings at a research location in Tifton, Ga. in the 1980's. Subsequently, in the late 1990's, the new variety was asexually propagated by softwood cuttings at that time in Griffin, Ga. The new variety was tested in plantings in Alapaha and Griffin, Ga. in the late 1990's. The selection was planted in ornamental trials at the Alapaha and Griffin, Ga. locations in 2011.

SUMMARY OF THE INVENTION

The new blueberry plant variety 'T-460' has not been observed under all possible environmental conditions. The phenotype may vary somewhat with variations in environment and cultural practices such as temperature and light intensity without, however, any variance in genotype.

The following traits have been repeatedly observed in the original plant and asexually propagated plants of the new variety, propagated by softwood cuttings and growing in Alapaha and Griffin Ga., and are determined to be the unique firmly fixed combinations of characteristics of the new blueberry plant variety 'T-460':

1. Very good color;
2. Good scar;
3. Large berry size;
4. Self-fruitfulness.

The new variety 'T-460' can be compared to the rabbiteye blueberry varieties 'Alapaha' (the subject of U.S. Plant Pat. No. 16,266) and 'Vernon' (the subject of U.S. Plant Pat. No. 18,291).

Comparison: The selection flowers and ripens after 'Alapaha' and 'Vernon' in the mid Georgia rabbiteye season. 'T-460' has large berries with good scar and very good color as compared to the standards 'Alapaha' and 'Vernon' in Alapaha and Griffin, Ga. over a 2-year period. 'T-460' has comparable berry firmness to 'Vernon' and larger berry size than 'Alapaha' (Tables 1 and 2). 'T-460' is moderately vigorous and aesthetically appealing. The parents 'T-223' and T-258' no longer exist and thus are not available for comparison. Data from years ago suggests that 'T-460' has a larger berry size than both parents. Both 'T-223' and 'T-258' were older breeding lines that are no longer in existence. However, 'T-460' has larger berry size than both of its parents.

Major attractions of 'T-460' are its ornamental appeal and suitability for home gardeners. Preliminary studies suggest that 'T-460' has considerable self-fruitfulness not demonstrated by previous rabbiteye varieties.

TABLE 1

2-year average ratings of some fruit and plant characteristics of 'T-460' and rabbiteye standard cultivars 'Alapaha' and 'Vernon' from 2013-2014 in field test plots at Alapaha, GA.

| Berry and plant | Alapaha location | | |
|---|---|---|---|
| attributes | 'Alapaha' | 'Vernon' | 'T-460' |
| Berry size | 6.3 | 8.0 | 8.3 |
| Berry scar | 7.0 | 7.0 | 7.3 |
| Berry color | 6.8 | 7.0 | 8.0 |
| Berry firmness | 7.0 | 7.5 | 7.5 |
| Berry flavor | 7.3 | 7.5 | 7.0 |
| Cropping | 6.0 | 5.0 | 6.0 |
| Plant vigor | 8.5 | 9.5 | 7.8 |
| Date of 50% flowering | March 24 | March 20 | March 23 |
| Date of 50% ripening | June 12 | June 10 | June 17 |
| Fruit development period (days) | 80 | 82 | 86 |

Rating scales are based on a 1 to 10 score, with 1 being the least desirable and 10 being the most desirable. A value of 6-7 is generally considered to be the minimum acceptable rating for a commercial cultivar. These plants were established in 2011.

TABLE 2

2-year average ratings of some fruit and plant characteristics of 'T-460' and rabbiteye standard cultivars 'Alapaha' and 'Vernon' (2013-2014) in field test plots at Griffin, GA.

| Berry and plant | Griffin location | | |
|---|---|---|---|
| attributes | 'Alapaha' | 'Vernon' | 'T-460' |
| Berry size | 6.5 | 8.3 | 8.4 |
| Berry scar | 7.0 | 7.3 | 7.3 |
| Berry color | 7.0 | 7.3 | 8.3 |
| Berry firmness | 6.8 | 7.5 | 7.8 |
| Berry flavor | 7.0 | 7.3 | 7.1 |
| Cropping | 6.0 | 6.0 | 7.3 |
| Plant vigor | 7.0 | 8.5 | 7.8 |
| Date of 50% flowering | April 3 | April 4 | April 6 |
| Date of 50% ripening | June 19 | June 23 | July 6 |
| Fruit development period (days) | 77 | 80 | 91 |

Rating scales are based on a 1 to 10 score, with 1 being the least desirable and 10 being the most desirable. A value of 6-7 is generally considered to be the minimum acceptable rating for a commercial cultivar. These plants were established in 2011.

BRIEF DESCRIPTION OF THE FIGURES

The accompanying photographic illustrations show typical four year old specimens of the new variety in full color of the foliage, flowering, and fruit of the new variety 'T-460'. The colors are as nearly true as is reasonably possible in a color representation of this type.

BOTANICAL DESCRIPTION

Figure 1:
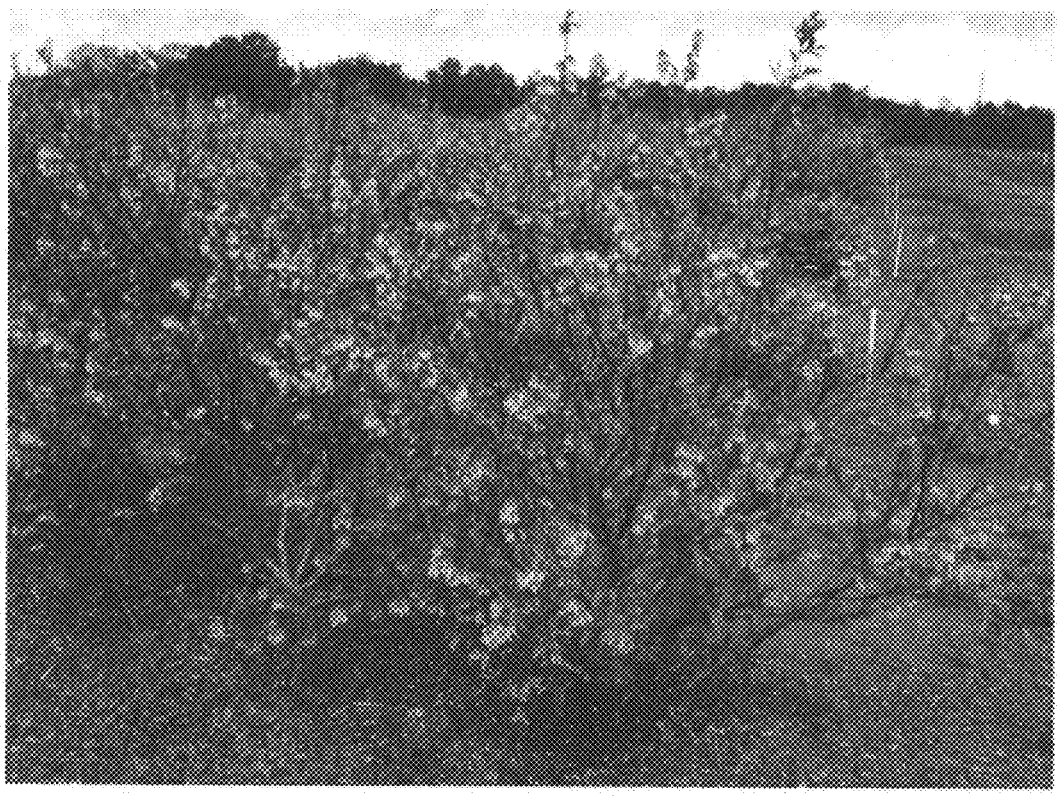
FIG. 1 is a photograph of the new variety 'T-460' during flowering in Griffin, Ga.
Figure 2:
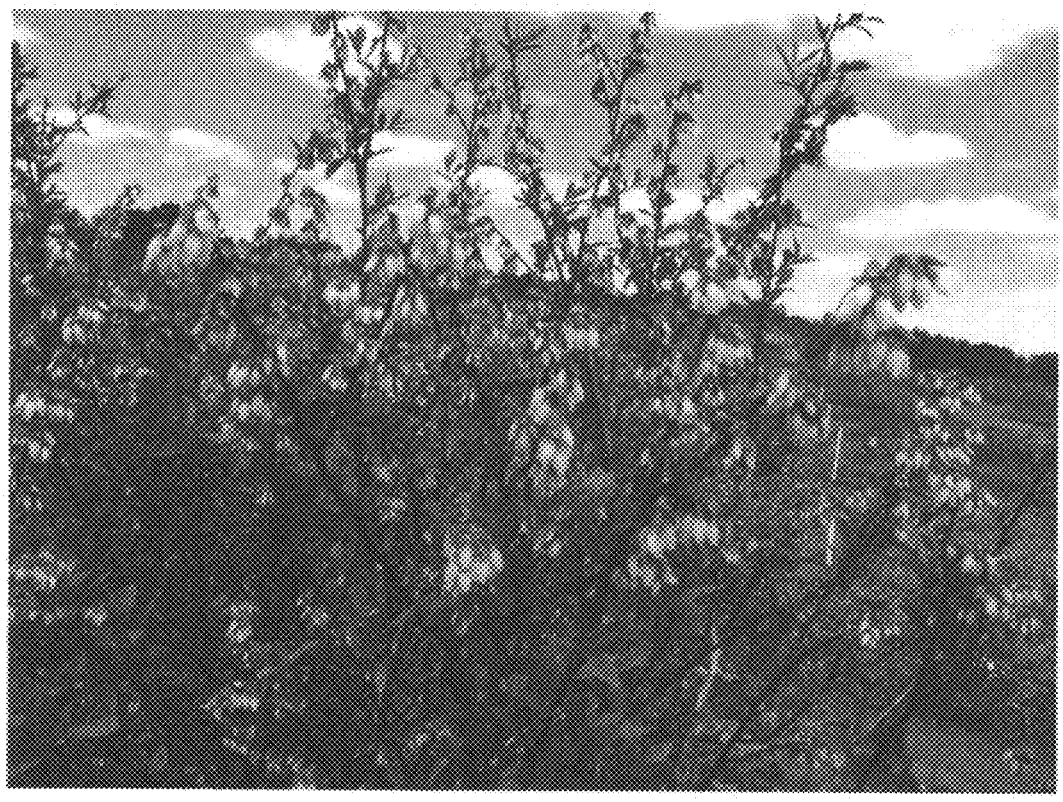
FIG. 2 is a close up photograph of the new variety 'T-460' during flowering in Griffin, Ga.
Figure 3:
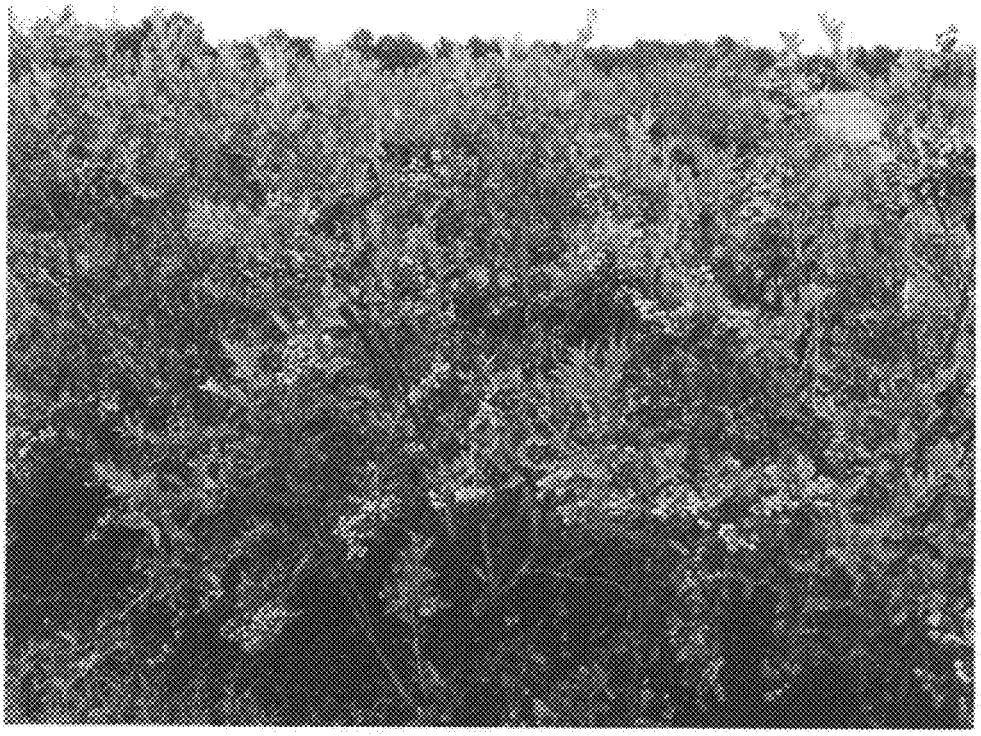
FIG. 3 is a photograph of new variety 'T-460' during fruit ripening in Griffin, Ga.
Figure 4:
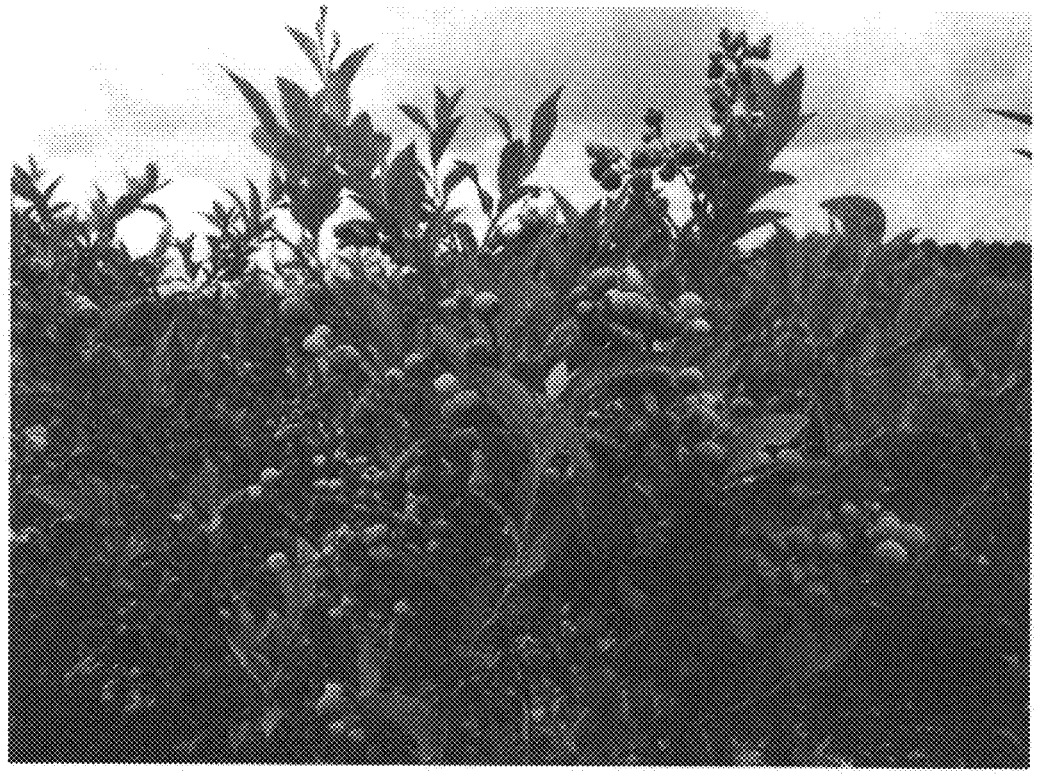
FIG. 4 is a close up photograph of the new variety 'T-460' fruit clusters.
Figure 5:
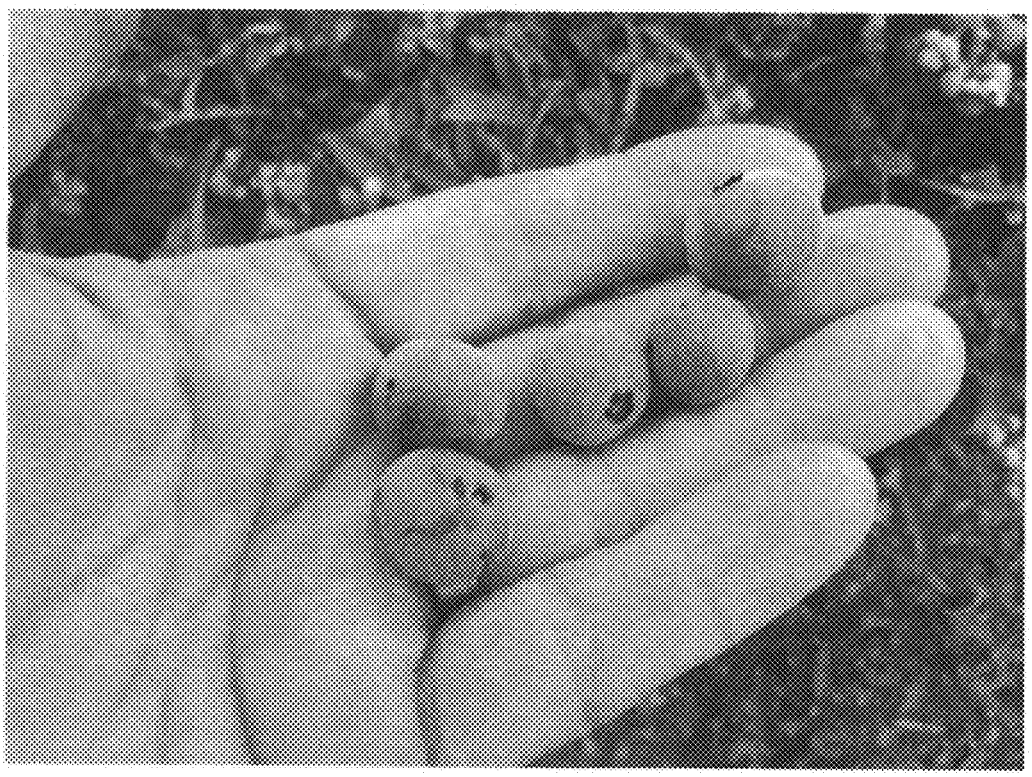
FIG. 5 is a close up photograph of typical fruit of the new variety 'T-460'.

Throughout this specification, color names beginning with a small letter signify that the name of that color, as used in common speech, is aptly descriptive. Color names beginning with a capital letter designate values based upon The Royal Horticultural Society Colour Chart, $5^{th}$ edition (R.H.S.) published by The Royal Horticultural Society, London, England.

The following is a detailed description of the botanical and pomological characteristics of the new variety 'T-460'. Where dimensions, sizes, colors, and other characteristics are given, it is to be understood that such characteristics are approximations and averages set forth as accurately as practicable. The descriptions reported herein are largely from observations of specimen plants grown in Alapaha and Griffin, Ga., with supplemental irrigation. The observed plants were about 3 to about 4 years old.

PLANT

Size: 1.2 to 1.4 m tall by about 4 years of age. The plant crown, or base, is narrow, typically 20 to 30 cm in diameter. The upper portion of plant canopy exceeds 1.3 to 1.5 m in diameter by 4 years.

Growth habit: Semi-spreading, with 2 to 3 main canes arising from the crown, and multiple branching of shoots (2 to 3 per cane) from those canes at 10 cm or less above the soil surface.

Growth: Moderately vigorous.

Productivity: Medium to high crop and yield, averaging 5 to 8 lbs of fruit per plant each year for plants 4 years and older grown under well-fertilized and irrigated field conditions.

Hardiness: Similar to other rabbiteye cultivars such as 'Alapaha' and 'Vernon'.

Chilling requirement: 500-550 hours of temperatures at or below 7° C. (about 45° F.) to induce normal leafing and flowering during the spring under conventional production systems.

Leafing: Plants tend to break sufficient leaf buds shortly after anthesis.

Canes:

*Diameter.*—25 to 40 mm for base of main canes that are about 4 years old and older; 20-25 mm first major branch diameter; 15 to 20 mm in 2 year old wood; 5 to 10 mm in current season wood.

*Color.*—Near Greyed-Green RHS 197C for base of canes that are about 4 years old and older; near Greyed-Brown 199C to Greyed-Green 197C for first major branch. Brown RHS 200D transitioning to Greyed-Brown RHS 199C in about 2 year old wood. Green 138D to Yellow-Green RHS 145C in current season wood.

Fruiting wood: Numerous twigs 15 to 20 cm in length, with internode lengths of 10-15 mm common.

Disease resistance: No exceptional disease resistance or susceptibility observed; typical for rabbiteye 'Alapaha' and 'Vernon'.

FOLIAGE

Leaf color: Healthy mature leaves.
*Top side.*—Green RHS N137D.
*Under side.*—Green RHS N138C.
Leaf arrangement: Alternate, simple.
Leaf shape: Elliptic.
Leaf surface: Both upper and lower surfaces are highly glaucous.
Leaf margins: Crenate, smooth.
Leaf venation: Pinnate, slightly reticulated.
Leaf apices: Narrowly acute.
Leaf bases: Cuneate.
Leaf dimensions:
*Length.*—55.0 to 65.0 mm.
*Width.*—20.0 to 25.0 mm.
Petioles: Small.
*Length.*—2.5 to 3.5 mm.
*Width.*—1.0 to 1.5 mm.
*Color.*—Yellow-Green RHS 145C.

FLOWERS

Date of 50% anthesis: March 23 in southeast Georgia and April 6 in middle Georgia (2-year average).
Flower shape: Urceolate.
Flower bud number: Medium to high, averaging 4 to 6 buds per fruiting shoot.
Flowers per cluster: 5 to 8 common.
Flower fragrance: None.
Corolla:
*Color.*—White RHS NN155C to White 155D (open flower). Red-Purple 62B blush often observed in corollas prior to opening.
*Length.*—8.5 to 10.0 mm.
*Width.*—4.5 to 5.5 mm.
*Aperture width.*—1.5 to 3.0 mm.
Flower peduncle:
*Length.*—15.0 to 20.0 mm.
*Color.*—Yellow-Green RHS 145B to Green RHS 138C.
Flower pedicel:
*Length.*—4.5 to 6.0 mm.
*Color.*—Green RHS 138C.
Calyx (with sepals):
*Diameter.*—5.0 to 6.0 mm.
*Color.*—Upper surface — Green RHS 138C. (Lower surface is the ovary, also Green FHS 138C).
Sepals:
*Number.*—Typically 5, being fused about half way down.
*Length.*—1.8 to 2.2 mm.
*Width.*—1.8 to 2.2 mm.
*Shape.*—More or less triangular.
*Apex.*—Typically occasionally some rounded ends are observed.
*Margins.*—Mostly smooth.
*Textures.*—Mostly smooth, both surfaces.
*Color.*—Green RHS 138C.
Stamen:
*Length.*—7.0 to 8.0 mm.
*Number per flower.*—10.
*Filament color.*—Green-White RHS 157B.
Style:
*Length.*—8.0 to 10.0 mm.
*Color.*—Yellow-Green RHS 145C.
Pistil:
*Length.*—10.0 to 12.0 mm.
*Ovary color (exterior).*—Green RHS 138C.
Anther:
*Length.*—4.0 to 4.8 mm.
*Number.*—10.
*Color.*—Greyed-Orange RHS 164A.
Pollen:
*Abundance.*—Medium.
*Color.*—Yellow-White RHS 158C.
Self-compatibility: The cultivar has a moderate degree of self-compatibility.

FRUIT

Date of 50% maturity: June 17 in southeast Georgia and July 6 in middle Georgia (2 year average).
Average harvest dates: First harvest June $10^{th}$ in South Georgia and June $20^{th}$ in Middle Georgia; second harvest June $17^{th}$ in South Georgia and July $6^{th}$ in Middle Georgia.
Fruit development period: 85 to 95 days.
Berry color:
*With wax.*—Violet-Blue RHS 98D to Blue 101C.
*With wax removed.*—Black RHS 202A.
Berry surface wax abundance: Very high.
Berry flesh color: Greyed-Green RHS 196D.
Berry weight:
*First harvest.*—2.2 g to 3.2 g.
*Second harvest.*—1.6 g to 2.0 g.
Berry size:
*Height from calyx to scar.*—14.0 to 17.0 mm.
*Diameter.*—16.0 to 20.0 mm.
Berry shape: Spherical.
Berry lusters: Typically 4 to 7 berries per cluster.
Fruit stem scar: Small, very dry, no tearing at harvest.
Calyx: Depth 1.0 to 2.5 mm; width 3.0 to 5.0 mm; sepals not highly visible, inward and flat when present.
Berry firmness: Very firm.
Berry flavor and texture: Very sweet, mildly acidic flavor, semi smooth texture.
Storage quality: Very good.
Suitability for mechanical harvesting: Not likely suitable.
Uses: Intended for home gardens and/or ornamental uses.

SEED

Seed abundance in fruit: Medium to high, with 15 to 20 fully developed seeds per berry.
Seed color: Greyed-Orange RHS 164A to 165B.
Seed dry weight: 47.6 mg per 100 seeds.
Seed size: 1.4 to 2.0 mm long; 0.4 to 0.7 mm wide for fully developed seeds.

What is claimed is:

1. A new and distinct variety of rabbiteye blueberry plant named 'T-460', substantially as illustrated and described herein.

* * * * *